United States Patent [19]

Fischer

[11] Patent Number: 4,956,074
[45] Date of Patent: Sep. 11, 1990

[54] MICROPROBE

[76] Inventor: Helmut Fischer, Industriestr. 21, 7032 Sindelfingen 6, Fed. Rep. of Germany

[21] Appl. No.: 390,238
[22] Filed: Aug. 4, 1989
[51] Int. Cl.$^5$ ............................................. G01N 27/26
[52] U.S. Cl. .................................................... 204/434
[58] Field of Search ................................. 204/434, 1 T

[56] References Cited

U.S. PATENT DOCUMENTS 4,310,389  1/1982  Harbulak ............................ 204/1 T
4,488,938  12/1984 Jirovsky et al. ..................... 204/1 T
4,560,464  12/1985 Lieber ................................. 204/434

Primary Examiner—G. L. Kaplan

[57] ABSTRACT

Measuring instruments for coulometrically measuring the thickness of metallic coatings pump the electrolyte from the first chamber 11 into the second chamber 12 and vice versa during the measurement. As a result, fresh electrolyte constantly reaches the measuring spot below the outlet orifice 7 and the troublesome formation of gas bubbles at this measuring spot is completely or substantially reduced. If the probe 3 is, however, inadvertently lifted off the coating 2, the pumped electrolyte spurts at high speed out of the outlet orifice 7. As a result, personnel and also material may suffer damage. The disposal presents difficulties. As a solution, provision is made for the entire system to employ underpressure and the maximum pressure occurring in chamber 11 or 12 is less than the external pressure. If the probe 3 is now inadvertently lifted during the measurement process, the electrolyte is sucked back into the first chamber 11 and/or the second chamber 12 and nothing is contaminated.

22 Claims, 3 Drawing Sheets

MICROPROBE

The invention relates to an apparatus for coulometric measurement of the thickness of metal coatings.

BACKGROUND OF THE INVENTION AND RELEVANT PRIOR ART

Such an apparatus has been disclosed by the older German Patent Application No. P 3,831,399.5. In that case there is an outer casting 1, an outlet orifice for an electrolyte at the bottom in the extension 6, an inner casing 3 in the first connection, a first and second connection in the first chamber 4 and in the second chamber 2, a nozzle pipe and a pump 7.

Depending on the position of the piston in the pump 7, electrolyte spurts in the measuring state, that is to say, with the exit orifice closed, first out of the nozzle pipe to the test specimen and then back into the chamber 4 or alternatively, the electrolyte rushes out of the chamber 4 towards the outlet orifice and towards the test specimen and is sucked back again through the nozzle pipe. The frequency of this flow is in the region of one hertz.

Whether it is acidic or basic, electrolyte is corrosive. In normal operation, it also does not escape from the probe. It has been found, however, that contrary to the operating instructions, the probe is lifted during the measuring process. This has the consequence that the electrolyte is very rapidly sprayed out of the outlet orifice, whether it is forced out of the first chamber or whether it is forced out of the second chamber.

The consequences of this can readily be imagined: the electrolyte is lost. The layer is attacked and is consequently perhaps unusable. Above all, however, the electrolyte may enter, for example, the eyes, the nose, the mouth or the like, of the operator and/or get onto his clothing which is then corroded.

Apparatus of the type described in the exemplary embodiments include an outer casing having at one end an outlet orifice for an electrolyte and a first connection for a pressure medium. The apparatus has an inner casing in the outer casing, a first chamber between the outer casing and the inner casing, a second chamber in the inner casing in a region thereof facing away from the outlet orifice and a second connection for a pressure medium that communicates with the second chamber. The apparatus also has a nozzle pipe that leads from the second chamber to the outlet orifice, with a debouchment situated inside the first chamber behind the outlet orifice, a pump having a connecting coupling connected to at least one of the connections by a pressure medium, which pump produces at least indirectly two different operating pressures, P0 and P1, for the first chamber and the second chamber, of which at least one of the operating pressures is oscillating.

OBJECT AND STATEMENT OF THE INVENTION

The object of the invention is to provide an apparatus in which no electrolyte escapes from the outlet orifice even if the probe is inadvertently lifted in the measurement mode.

According to the invention, this object is achieved by the following features: a valve apparatus is provided between the pump and the microprobe, wherein in a working position of the pump and the valve apparatus an underpressure P2, which is substantially lower than the maximum operating pressures of P0 and P1, is superimposed on at least one of the operating pressures. As a result of the powerful underpressure around which the operating pressures P0 and P1 oscillate all the electrolyte is sucked back and does not leave either the first chamber or the second chamber. This achievement may be compared with a pulsating direct current in which electrons also flow to and fro. To that extent identical conditions exist for alternating current. The direct current added to the true alternating current—here the first underpressure—is, however, high enough for an adequate spacing from the X-axis if the relationships are plotted in cartesian coordinates.

The preferred exemplary embodiment includes the following additional advantageous features, which relate to how the pressure relationships can be produced.

The pump produces the lowermost pressure P2 as a constant pressure that is present at the connecting coupling; a first line is situated between the connecting coupling and one of the connections associated with the chambers; a first valve is situated in the first line; and the first valve has a second inlet for a pressure medium that has a pressure in the region of 0, which second inlet can be periodically opened and closed. As a result, the pump has to produce only underpressure and it is possible to produce the varying pressure only in the first line. To produce the underpressure, pumps used in quantity, for example, from aquarian technology can be employed.

The pressure medium is air. As a result, the apparatus can be operated in normal ambient air since the electrolytes do not oxidize in air.

P0 and P1 are underpressures. As a result the electrolyte is sucked back even at the pressure P1.

The second inlet of the first valve can be opened and closed by means of a needle valve. This makes it possible to control the underpressures very finely.

A dust-proof filter is connected upstream of the needle valve. This ensures that the needle is not impaired in its operation and the operating conditions are maintained over a long period.

A second line is situated between the connection of the second chamber and the connecting coupling, and the flow resistance between the connection of the second chamber and the connecting coupling is less than in the first line. As a result the electrolyte is sucked back only into one chamber and it is only necessary to deal with trapping electrolytes therein and possibly in the downstream line.

One chamber is the first chamber and another chamber is the second chamber. As a result, the to-and-fro flow of the electrolyte can be controlled better because the area affected by the pressure is larger in the first chamber.

The outlet orifice is so small that it has capillary action with respect to the electrolyte. As a result, no electrolyte can flow out of the probe with the pump switched off.

An electrolyte trap is provided between the second chamber and the second line. As a result the electrolyte sucked back with high kinetic energy does not under any circumstances reach the pump and is also trapped even before reaching any valve that may be present and arranged in the second line. Should electrolyte also be sucked out of the first chamber, and apparatus for trapping the electrolyte would also have to be provided there.

Additional advantageous features of the described embodiment include:

The trap has a baffle plate in a continuation of the nozzle pipe for electrolyte that has been sucked back, and at least one opening for pressure medium is provided towards a termination of the baffle plate outside of the continuation of the nozzle pipe and outside of the electrolyte repelled by the baffle plate.

The baffle plate is concave towards the nozzle pipe.

The baffle plate has a sharp edge directed towards the nozzle pipe.

The baffle plate is arranged coaxially with an edge spacing with respect to the second chamber.

A third chamber into which the opening for pressure medium debouches is provided behind the second chamber.

The opening for pressure medium debouches at the lowest point of the third chamber when the probe is held vertically.

A rear side of the baffle plate is at a distance from a roof the second chamber and the opening for pressure medium starts behind the rear side of the baffle plate.

The baffle plate projects by means of an extension into a hole in the roof of the second chamber.

The opening for pressure medium is provided in the region of the hole.

The opening for pressure medium is provided in a region of a circumference of the extension.

The second chamber merges from the baffle plate into an enlarged section.

A second valve is situated in the second line, wherein the trap is a vessel trap that is situated in the second line and in front of the second valve.

An apparatus, which does not, however, fulfill all the known features of the present invention is described in U.S. Pat. No. 4,488,938. A likewise related probe is described in the German Patent Specification No. 3,046,198, FIG. 1 and 2. These publications also provide the background to the technology described here.

DESCRIPTION OF THE DRAWINGS

A preferred exemplary embodiment is now described. In the drawing.

DETAILED DESCRIPTION OF PREFERRED EXEMPLARY EMBODIMENT

Figure 1:
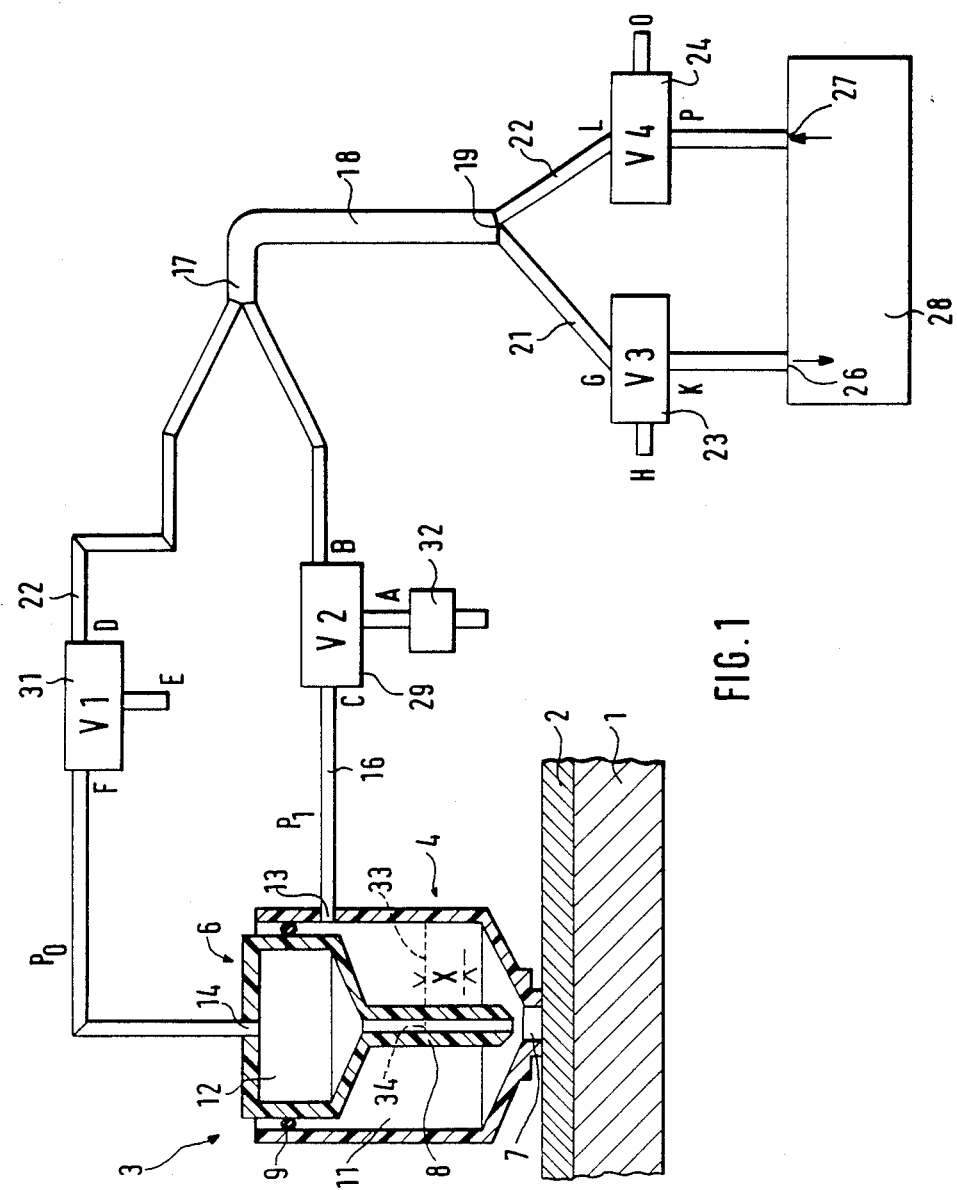
FIG. 1 shows the diagrammatic view of a circuit.
Figure 2:
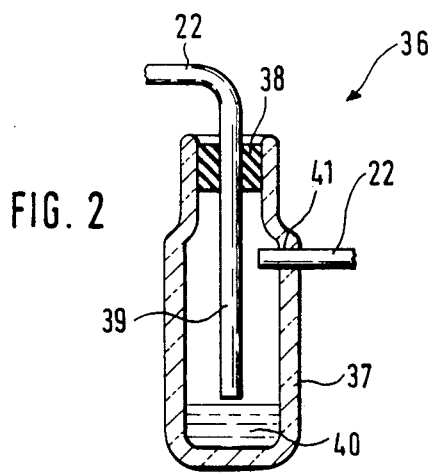
FIG. 2 shows a trapping vessel in section.

Deposited on a base material 1 is a metallic layer 2. A probe 3 has an outer casing 4 and an inner casing 6, both essentially of plastic. The outer casing 4 has an outlet orifice 7 at the bottom. The inner casing 6 merges at the bottom into a nozzle pipe 8. Outer casing 4 and inner casing 6 are sealed in an airtight and liquidtight manner with a seal 9 which is indicated diagrammatically. A first chamber 11 is provided between the outer casing 4 and the inner casing 6 for the nozzle pipe 8 respectively, and a second chamber 12 is provided in the inner casing 6 including the pipe 8. A first connection 13 is provided on the outer casing 4 at the upper end region of the chamber 11 and a further connection 14 is provided in the upper region of the chamber 12 of the inner casing 6. A first line 16 runs from connection 13 to a branching point 17 from which a pipe 18 runs to a further branching point 19. This bifurcates into a line 21 and a line 22. In the line 21 there is a valve 23 and in the line 22 there is a valve 24. The line 21 runs to an intake coupling 26 and the line 22 to a pressure coupling 27 of a pump 28.

In the line 16 there is a valve 29 and in the line 22 there is a valve 31.

The valve 23 can be connected from K to G, with the result that the intake coupling 26 is connected via the line 21, the line 18 and the branching point 17 to the lines 16, 22 on the right of the valves 29, 31. The coupling H—that is to say, the ambient pressure—may, however, also be connected to the output G so that ambient pressure exists in 21, 18, 17 and the right-hand region of 16, 22.

The valve 24 may analogously be connected from P to L or from O to L.

The valve 31 may be connected from F to D or from F to E (ambient pressure).

The connections in the valves 23, 24, 31 are open-closed connections.

Figure 3:
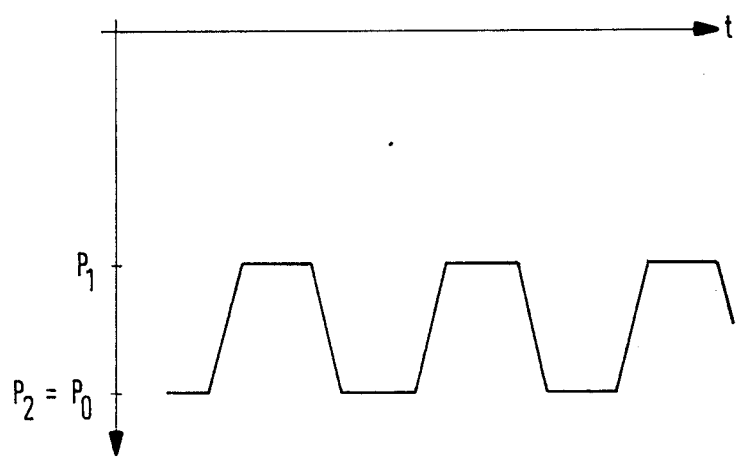
FIG. 3 shows a diagram of the pressure in the first chamber.

An air filter 32 is, however, connected upstream of the coupling A of the valve 29. In addition, the valve 29 is constructed as a needle valve. In this case, the point of a needle is able to seal, in a manner known per se, a needle seating to a greater or lesser extent. Such a structure makes it possible to adjust finely the pressure $P_1$ from FIG. 3. The needle valve is able to effect a venting, i.e. to produce a connection between A (ambient pressure) and C which is unobstructed to a greater or lesser extent and lasts for along period. In the extreme case, if no connection at all existed, $P_1$ would be at $P_0$, that is to say, no oscillating movement would take place. In the other extreme case, the needle valve opens completely at every stroke, with the result that there is a passage between A and C and then $P_1$ would be close to the t-axis of FIG. 3 with a slight underpressure. Somewhere in between is the optimum, which results in the liquid level 33 oscillating in the chamber 11 and the liquid level 34 oscillating in the nozzle pipe 8 always only, for example, with the amplitude X and in the chamber 11 never becoming completely empty or quite full and also the chamber 12 never becoming quite empty or full, because air instead of electrolyte would, after all, otherwise enter the outlet orifice 7. Depending on whether the needle of the valve 29 is closed to a greater or lesser extent, the amplitude X is greater or smaller.

The operating modes are as follows:

Charging the second chamber 12 with electrolyte: lower part of the measuring cell is immersed in the electrolyte stock container.

Pump sucks. Valve 29 in the C-A position. Valve 31 in the F-D position. Electrolyte is sucked from the stock container through the outlet orifice 7 into chamber 12.

Charging probe 3, and specifically, to the same level as chamber 11 and 12: Valve 31 in F-D position, valve 29 in C-B position, pump 28 sucking, liquid levels 33, 34 of the electrolyte at the same level.

Measurement: Valve 29 is alternatively set to C-B and C-A position. Valve 31 is in the F-D position. The pump 28 is sucking.

Normal termination: Discontinue alternating operation of valve 29, that is to say set it to C-B position. Valve 31 in E-D position; electrolyte flows into chamber 12. Valve 29 is now switched for a short time to C-A which reduces the underpressure 11. The electrolyte now flows into chamber 12.

Inadvertent lifting during the measurement: Pump 28 is running, valve 29 switches alternately between C-B and C-A. Atmospheric pressure enters the outlet orifice 7. Because of the higher flow resistance imposed on the flow, substantially less air flows out of the connection 13 than out of the connection 14. The electrolyte contained in the chamber 12 is sucked upwards and additionally, also the electrolyte contained in the chamber 11. This is further promoted by the fact that the debouchment 43 of the nozzle pipe 8 is just above the outlet orifice 7 and electrolyte flowing downwards out of the chamber 11 has to flow past the debouchment 43.

Emptying electrolyte: Valve 29 in C-A position, valve 23 in H-K position, valve 31 in F-D position, valve 24 in L-P position. Pump 28 on. Electrolyte flows out of chamber 12. During the remaining operation, valve 24 is, of course, in P-O position.

Flushing chamber 12: As operating modes for charging with, and emptying, electrolyte.

The apparatus is therefore not only capable of a large number of operating modes. On the contrary, it also copes with the inadvertent lifting of the probe 3.

Figure 4:
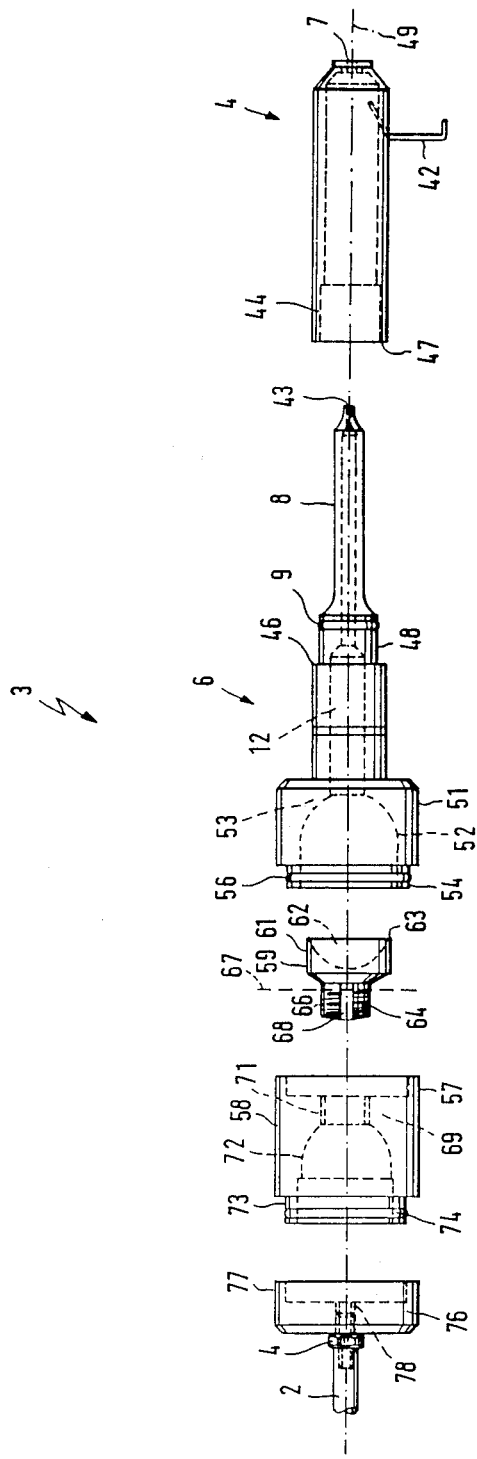
FIG. 4 shows a measuring cell which has actually been constructed.

If the probe 3 is inadvertently lifted, the electrolyte shoots upwards with high energy. If measures yet to be explained with reference to FIG. 4 are no sufficiently effective, and the electrolyte threatens to enter the line 22 and consequently reach the valve 31, a trapping bottle 36 may be provided in the line 22 to the left of the valve 31. A bottle 37 is sealed at the top with a plug 38 through which a down pipe 39, which terminates at some distance above the bottom, is passed in an airtight manner. An airtight leadthrough 41 is provided substantially higher than the lower debouchment of the down pipe 39. The debouchment of the down pipe 39 is at an appreciable distance from the leadthrough 41, with the result that, even with a high backflow rate, accumulated electrolyte 40 does not enter the leadthrough 41 and consequently the pipe 22.

The drawing of FIG. 4 reveals the outer casing 4, the inner casing 6 with the nozzle pipe 8, the seal 9, the connection 13 and 14, the chamber 12 and the outlet orifice 7, and also the line 22. Attached to and led through the outer casing 4 is an electrode 42, which corresponds to the electrode 33 from the German Patent Specification No. 3,046,198. Auxiliary circuitry, known in the art, is associated with the probe 3. If the outer casing 4 is attached to the inner casing 6, the debouchment 43 of the nozzle pipe 8 is situated on the left and concentrically in front of the outlet orifice 7.

A left-hand end edge 44 then sits in an airtight and liquid-tight manner on a collar 46 of the internal casing 6 and its left-hand end face 47 abuts an annular surface 48. The probe 3 is essentially of axially symmetrical construction with respect to the geometrical longitudinal axis 49. The internal casing 6 merges on the left into a widened section 51 which is also axially symmetrical and which incorporates a relatively large cup 52 which is open to the left and which communicates with the chamber 12. The cup 52 has a concave bottom 53, with the result that if the probe 3 is in the vertical position, any electrolyte which enters the cup 52 is able to drain rapidly and without residue into the chamber 12. On the left of the enlargement 51 an annular flange 54 is provided which as an O-ring 56 embedded in its external circumference. The annular flange 54 can be inserted into a circumferential flange 57 of a connecting piece 58 to form a seal. Together with the cup 52, the connecting piece 58 represents an electrolyte trap. Associated with the connecting piece 58 is a separate screw insert 59 which has a cylindrical head 61 whose outside diameter is less than the inside diameter of the cup 52. The cylindrical head 61 has a concave recess 62 which is directed towards the right and which merges into a sharp edge 63 on the right. Substantially smaller in diameter than the cylindrical head 61 is a short threaded shank 64 which points to the left and which has an external thread 66. The latter extends, however, only up to the line 67, with the result that the threaded shank 64 cannot be fully screwed in. Incorporated over the entire length of the threaded shank 64 are two grooves 68 which are diametrically opposite each other and which are continuous from left to right and still continue even to the right of the line 67. The circumferential flange 57 is followed to the left by a bottom 69 which incorporates a threaded hole 71 and into which the external thread 66 can be screwed in up to the line 67. The bottom 69 is again followed on the left by a cup 72 and an annular flange 73 which supports an O-ring 74 let in from the outside and which is precisely equal in size to the annular flange 54 and the O-ring 56 with the result that a cover 76 can be mounted so as to form a seal directly on the widened section 51 if there is no desire to sue the connecting piece 58. The cover 76 has a circumferential flange 77 which fits in an airtight and liquid-tight manner on the annular flange 73. It has a central through hole 78 which debouches into connection 14 which, according to FIG. 4, has the shape of a nipple.

Normally, the probe 3 is held vertically or approximately vertically, as is shown in FIG. 1 of U.S. Pat. No. 4,488,938.

If the exit orifice 7 is now lifted inadvertently during measurement, the debouchment 43 sucks an electrolyte into the chamber 12 owing to the powerful underpressure $P_2$. The kinetic energy is, however, so high that the electrolyte does not remain in the chamber 12, but shoots up in the cup 52. Because the cup 52 is larger in diameter than the chamber 12, an expansion is first of all able to take place and this dissipates some of the kinetic energy of the electrolyte. Despite this, liquid continues to rush into the recess 62 and is then deflected downwards by the latter. The liquid deflected downwards continues to retard the rising liquid. The liquid is able to calm down in the cup 52 and flow back again into the chamber 12. Because the grooves 68 are on the sheltered side of the electrolyte fountain because of the cylindrical head 61, the powerful underpressure is nevertheless fed through the grooves 68 from the line 22 into the cup 52 and no electrolyte reaches the line 22. The sharp edge 63 forms a separation edge for the deflection process.

The invention also makes it readily possible to put electrolytes of different types into use. For this purpose, the outside casing 4 remains held at the measurement point, for example, by a frame. The inside casing 6 drawn on the left in FIG. 4 is separated from the line 22 by means of its connection 14 and is replaced by an identical inner casing 6 which contains a different electrolyte or fresh electrolyte and which is connected to the connection 14. The nozzle pipe 8 is inserted until 46 and 47 make contact.

I claim:

1. In an apparatus for a microprobe (3) for coulometric measurement of the thickness of metallic coatings (2), comprising
an outer casing (4) having at one end an outlet orifice (7) for an electrolyte used in coulometric measurement and a first connection (16) for a pressure medium, an inner casing (6) in the outer casing (4),
a first chamber (11) between the outer casing (4) and the inner casing (6),
a second chamber (12) in the inner casing (6), in a region thereof facing away from the outlet orifice (7),
a second connection (14) for a pressure medium that communicates with the second chamber (12),
a nozzle pipe (8) that leads from the second chamber (12) to the outlet orifice (7) and has a debouchment (43) situated inside the first chamber (11) behind the outlet orifice (7),
first pump means (28, 17, 16) having a connecting coupling (17) connected to at least one of the connections (13, 14) by a pressure medium means (16), which first pump means produces at least indirectly at least one of two different operating pressures, P0 and P1, for at least one of the chambers of which at least one of the operating pressures is oscillating,
second pump means (28, 17, 22) for producing at least indirectly the second of the two different operating pressures P0 and P1 for the other chamber
the improvement wherein:
a valve apparatus (29, 31, 23, 24) is provided between the first and second pump means and the microprobe (3), wherein in a working position of the first and second pump means and the valve apparatus (29, 31, 23, 24) an underpressure P2, which is substantially lower than the maximum operating pressures of P0 and P1, is superimposed on at least one of the operating pressures.

2. The apparatus as claimed in claim 1, wherein the first pump means produces the lowermost pressure P2 as a constant pressure that is present at the connecting coupling, the pressure medium means comprises a first line situated between the connecting coupling and one of the connections associated with the chambers, a first valve is situated int he first line, and the first valve has a second inlet for a pressure medium that has a pressure in the region of 0, which second inlet can be periodically opened and closed.

3. The apparatus as claimed in claim 2, wherein the second inlet of the first valve can be opened and closed by means of a needle valve.

4. The apparatus as claimed in claim 3, wherein a filter is connected upstream of the needle valve to filter the pressure medium passing through the needle valve.

5. The apparatus as claimed in claim 1, wherein the pressure medium means conveys gas.

6. The apparatus as claimed in claim 1, wherein the first and second pump means are arranged to produce operating pressures P0 and P1 that are underpressures.

7. The apparatus as claimed in claim 1, wherein a second line is situated between the connection of the second chamber and the connecting coupling, and the flow resistance between the connection of the second chamber and the connecting coupling is less than in the first line.

8. The apparatus as claim in claim 7, wherein an electrolyte trap is provided between the second chamber and the second line.

9. The apparatus as claimed in claim 8 comprising a second valve situated in the second line, wherein the trap is a vessel trap that is situated in the second line and in front of the second valve.

10. The apparatus as claimed in claim 8, comprising a nozzle pipe, wherein the trap has a baffle plate in a continuation of the nozzle pipe for electrolyte that has been sucked back, and at least one opening for pressure medium is provided towards a termination of the baffle plate outside of the continuation of the nozzle pipe and outside of the electrolyte repelled by the baffle plate.

11. The apparatus as claimed in claim 10, wherein the baffle plate is concave towards the nozzle pipe.

12. The apparatus as claimed in claim 11, wherein the baffle plate has a sharp edge directed towards the nozzle pipe.

13. The apparatus as claimed in one of claims 10-12, wherein the baffle plate is arranged coaxially with an edge spacing with respect tot he second chamber.

14. An apparatus as claimed in one of claims 10-12, wherein a third chamber into which the opening for pressure medium debouches is provided behind the second chamber.

15. The apparatus as claimed in claim 14, wherein the opening for pressure medium debouches at the lowest point of the third chamber when the probe is held vertically.

16. The apparatus as claimed in claim 10-12, wherein a rear side of the baffle plate is at a distance from a roof of the second chamber and the opening for pressure medium starts behind the rear side of the baffle plate.

17. The apparatus as claimed in claim 16, wherein the baffle plate projects by means of an extension into a hole in the roof of the second chamber.

18. The apparatus as claimed in claim 17, wherein the opening for pressure medium is provided in the region of the hole.

19. The apparatus as claimed in claim 17, wherein the opening for pressure medium is provided in a region of a circumference of the extension.

20. The apparatus as claimed in claim 16, wherein the second chamber merges from the baffle plate into an enlarged section.

21. The apparatus as claimed in claim 1, wherein the first chamber is connected to a first pressure medium means for receiving a higher pressure and the second chamber is connected to a second pressure medium means for receiving a lower pressure.

22. The apparatus as claimed in claim 1, wherein the outlet orifice is a capillary tube.

* * * * *

UNITED STATES PATENT AND TRADEMARK OFFICE
CERTIFICATE OF CORRECTION

PATENT NO. : 4,956,074

DATED : September 11, 1990

INVENTOR(S) : Fischer

It is certified that error appears in the above-identified patent and that said Letters Patent is hereby corrected as shown below:

Column 6, Claim 1, line 6, after "connection" correct "16" to read --13--.

Signed and Sealed this

Third Day of March, 1992

Attest:

HARRY F. MANBECK, JR.

*Attesting Officer*    *Commissioner of Patents and Trademarks*